(12) United States Patent
Famodu et al.

(10) Patent No.: US 6,852,910 B1
(45) Date of Patent: Feb. 8, 2005

(54) PLANT RECOMBINATION PROTEINS

(76) Inventors: Omolayo O. Famodu, 216 Barrett Run Pl., Newark, DE (US) 19702; Michele Morgante, 2306 Lorelei La., Wilmington, DE (US) 19810

( * ) Notice: Subject to any disclaimer, the term of this patent is extended or adjusted under 35 U.S.C. 154(b) by 0 days.

(21) Appl. No.: 09/958,650

(22) PCT Filed: May 9, 2000

(86) PCT No.: PCT/US00/12587

§ 371 (c)(1),
(2), (4) Date: Oct. 10, 2001

(87) PCT Pub. No.: WO00/68390

PCT Pub. Date: Nov. 16, 2000

Related U.S. Application Data
(60) Provisional application No. 60/133,438, filed on May 11, 1999.

(51) Int. Cl.[7] .......................... A01H 1/00; C07H 21/04; C07K 14/415; C12N 5/14; C12N 9/00
(52) U.S. Cl. ..................... 800/295; 435/6; 435/69.1; 435/468; 435/419; 435/252.3; 435/320.1; 530/370; 536/23.6; 800/278
(58) Field of Search ................... 435/6, 69.1, 70.1, 435/91.4, 468, 183, 410, 419, 252.3, 320.1; 530/370; 536/23.2, 23.6; 800/278, 295

(56) References Cited

FOREIGN PATENT DOCUMENTS

| WO | WO 87/01730 A1 | 3/1987 |
|---|---|---|
| WO | WO 93/22443 A1 | 11/1993 |
| WO | WO 97/41228 A2 | 11/1997 |
| WO | WO 99/41394 A1 | 8/1999 |

OTHER PUBLICATIONS

Morita et al., "A mouse homolog for the *Escherichia coli* recA and *Saccharomyces cerevisiae* RAD51 genes," Proc. Natl. Acad. Sci. USA, vol. 90, pp. 6577–6580, Jul. 1993.
Akira Shinohara et al., Nature genetics, vol. 4:239–243, 1993, Cloning of human, mouse and fission yeast recombination genes homologous to RAD51 and recA.
Victor I. Klimyuk et. al., The Plant Journal, vol. 11:1–14, 1997, AtDMC1, The Arabidopsis Homologue of the Yeast DMC1 Gene: Characterization, Transposon–Induced Allelic Variation and meiosis–associated expression.
Yukang Lin et. al., Genetics, vol. 136:769–779, 1994, Transient, Meiosis–induced Expression of the REC6 and REC12 Genes of Schizosaccharomyces Pombe.
Stephen C. Kowalczykowski et al., Annu. Rev. Biochem., vol. 63:991–1043, 1994, Homologous Pairing and DNA Strand–Exchange Proteins.
Patrick Sung, Science, vol. 265:1241–1243, 1994, Catalysis of ATP–dependent homologous DNA Pairing and Strand Exchange by Yeast RAD51 Protein.
Roland Kanaar et. al., Nature, vol. 391:335–338, 1998 From Competition to Collaboration.
Fiona E. Benson et. al., Nature, vol. 391:401–404, 1998, Synergistic Actions of RAD51 and RAD52 in Recombination and DNA Repair.
National Center for Biotechnology Information General Identifier NO: 1706947, Dec. 4, 1996, Smith, K.N. et. al.
National Center for Biotechnology Information General Identifier NO: 4886752, Apr. 24, 2001, Franklin, A.E. et. al. Three–Dimensional Microscopy of the RAD51 Recombination Protein During Meiotic Prophase.
Amie E. Franklin et al., Plant Cell, vol. 11:809–824, 1999, Three–Dimensional Microscopy of the Rad51 Recombination Protein during Meiotic Prophase.
Natalie Yeager Stassen et. al., Curr Genet., vol. 31:144–157, 1997, Isolation and Characterization of RAD51 Orthologs from *Coprinus Cinereus* and *Lycopersicon Esculentum*, and Phylogenetic Analysis of Eukaryotic RECA Homologs.
EMBL Sequence Library Database Accession NO: U43528, Dec. 13, 1996, Smith K. N. et. al., Arabidopsis Thaliana RAD51 Homolog.

*Primary Examiner*—Phuong T. Bui
(74) *Attorney, Agent, or Firm*—Morgan & Finnegan, L.L.P.

(57) ABSTRACT

This invention relates to an isolated nucleic acid fragment encoding a recombination protein. The invention also relates to the construction of a chimeric gene encoding all or a substantial portion or the recombination protein, in sense or antisense orientation, wherein expression of the chimeric gene results in production of altered levels of the recombination protein in a transformed host cell.

10 Claims, 2 Drawing Sheets

FIGURE 1A

```
              *         *    *  * *  *** * ***  *    ******      *     *** * *** *
SEQ ID NO:02  MSATMEQQRHQKAPQQQDEAEEIQPGPLPVEQLQASGIAATDVKKLKDAGICTVESVAYT
SEQ ID NO:08  MSSAAAHQKAAAAAPVEEE-EAGEHGPFPIEHLQASGIAAVDVKKLKDAGLCTVESVAYS
SEQ ID NO:09  MT-TMEQRRNQNAVQQQDD-EETQHGPFPVEQLQAAGIASVDVKKLRDAGLCTVEGVAYT
SEQ ID NO:10  MSSAAQQQQKAAAA---EQ-EEVEHGPFPIEQLQASGIAALDVKKLKDSGLHTVEAVAYT
              1                                                           60

************ **  *******  ****** ***     *   ************ ***
SEQ ID NO:02  PRKDLLQIKGISEAKVDKIIEAASKLVPMGFTSASELHAQRDAIIQITTGSRELDKILEG
SEQ ID NO:08  PRKDLLQIKGISEAKVDKIIEAASKLVPLGFTSATQLHAQRLEIIQVTTGSRELDKILEG
SEQ ID NO:09  PRKDLLQIKGISDAKVDKIVEAASKIVPLGFTSASQLHAQRQEIIQITSGSRELDKVLEG
SEQ ID NO:10  PRKDLLQIKGISEAKADKIIEAASKIVPLGFTSASQLHAQRLEIIQVTTGSRELDKILEG
              61                                                         120

*  ********* ********* *******       ************  ********
SEQ ID NO:02  GVETGSITELYGEFRSGKTQLCHTLCVTCQLPLDQGGGEGKAMYIDAEGTFRPQRLLQIA
SEQ ID NO:08  GIETGSITELYGEFRSGKTQLCHTLCVTCQLPLDQGGGEGKALYIDAEGTFRPQRLLQIA
SEQ ID NO:09  GIETGSITELYGEFRSGKTQLCHTLCVTCQLPMDQGGGEGKAMYIDAEGTFRPQRLLQIA
SEQ ID NO:10  GIETGSITEIYGEFRSGKTQLCHTPCVTCQLPLDQGGGEGKALYIDAEGTFRPQRLLQIA
              121                                                        180

********  *********************     ************ *********
SEQ ID NO:02  DRFGLNGVDVLENVAYARAYNTDHQSRLLLEAASMMVETRFAVMIVDSATALYRTDFSGR
SEQ ID NO:08  DRFGLNGADVLENVAYARAYNTDHQSRLLLEAASMMVETRFALMVIDSATALYRTDFSGR
SEQ ID NO:09  DRFGLNGADVLENVAYARAYNTDHQSRLLLEAASMMIETRFALLIVDSATALYRTDFSGR
SEQ ID NO:10  DRFGLNGADVLENVAYARAYNTDHQSRLLLEAASMMIETRFALMVVDSATALYRTDFSGR
              181                                                        240
```

FIGURE 1B

```
                   *********** * ***** ** ***** **** * ***** *************
SEQ ID NO:02       GELSARQMHLAKFLRSLQKLADEFGVAIVITNQVVSQVDGSAVFAGPQIKPIGGNIMAHA
SEQ ID NO:08       GELSARQMHLAKFLRSLQKLADEFGVAVVISNQVVAQVDGGAMFAGPQIKPIGGNIMAHA
SEQ ID NO:09       GELSARQMHLAKFLRSLQKLADEFGVAVVITNQVVAQVDGSALFAGPQFKPIGGNIMAHA
SEQ ID NO:10       GELSARQMHMAKFLRSLQKLADEFGVAVVITNQVVAQVDGSAMFAGPQFKPIGGNIMAHA
                   241                                                       300

**** ****** ******** ****** ******** ** * *** **
SEQ ID NO:02       TTTRLALRKGRGEERICKVISSPCLAEAEARFQICAEGVSDVKD
SEQ ID NO:08       STTRLYLRKGRAEERICKVVSSPCLAEAEARFQISPEGVTDVKD
SEQ ID NO:09       TTTRLALRKGRAEERICKVISSPCLPEAEARFQISTEGVTDCKD
SEQ ID NO:10       STTRLALRKGRGEERICKVISSPCLAEAEARFQLASEGIADVKD
                   301                                      344
```

PLANT RECOMBINATION PROTEINS

This application claims the benefit of U.S. Provisional Application No. 60/133,438, filed May 11, 1999.

FIELD OF THE INVENTION

This invention is in the field of plant molecular biology. More specifically, this invention pertains to nucleic acid fragments encoding recombination proteins in plants and seeds.

BACKGROUND OF THE INVENTION

Transgenic plant product development by conventional transformation and breeding efforts is a slow and unpredictable process. Gene targeting systems can overcome problems with expression variability, unpredictable impacts of random gene insertion on agronomic performance, and the large number of experiments that need to be conducted. Such systems can also provide approaches to manipulating endogenous genes. Of course, targeting system requires the ability to focus the recombination process to favor recovery of desired targeting events.

Recombination is the process by which DNA molecules are broken and rejoined, giving rise to new combinations. It is a key biological mechanism in mediating genetic diversity and DNA repair. Much research has focused on describing the process, since it is an integral biological phenomenon and as such, forms the basis of a number of practical applications ranging from molecular cloning to introduction of transgenes.

The natural cellular DNA repair and recombination machinery consists of a complex array of protein components interacting in a highly controlled manner to ensure that the fidelity of the genome is conserved throughout the many internal events or external stimuli experienced during each cell cycle. The ability to manipulate this machinery requires an understanding of how specific proteins are involved in the process, and how the genes that encode those proteins are regulated. Since the primary approaches to gene targeting involve recombinases, whether operating in their natural in vivo environment (as during normal recombination) or as part of schemes that involve pretreatment of substrates-so as to associate DNA with a recombinase and increase the efficiency of targeting (e.g. double D-loop), there is a continuing need to isolate and characterize the genes for these molecules. Because many different protein components may be involved in gene targeting, the availability of host-specific genes and proteins could aid in avoiding possible problems of incompatibility associated with molecular interactions due to heterologous components.

A number of proteins involved in recombination have been isolated and the corresponding genes have been cloned, including RecA of *E coli*, a key player in the recombination process. RecA catalyzes the pairing up of a DNA double helix and a homologous region of single-stranded DNA, and so initiates the exchange of strands between two recombining DNA molecules. It exhibits DNA-dependent ATPase activity, binding DNA more tightly when it has ATP bound than when it has ADP bound. RecA gene homologues in other organisms have been isolated, including RAD51 from human, mouse, corn, and yeast (Shinohara, A. et al., (1993) *Nat. Genet.* 4:239–243; PCT published Patent Application No. WO 99/41394-A1), and DMC1 from yeast, lily, and *Arabidopsis* (Klimyuk, V. I. and Jones, J. D., (1997) *Plant J.* 11:1–14). In fission yeast, a number of meiotic recombination genes have been identified by genetic complementation, including rec6 and rec12 (Lin, Y. and Smith, G. R., (1994) *Genetics* 136:769–779).

Sequences for the bacterial RecA recombinase and functional homologs from yeast and several animal species have been disclosed in various publicly accessible sequence databases. Numerous publications characterizing these recombinases exist (see, e.g., Kowalczykowski et al., *Annu. Rev. Biochem.*, 63:991–1043 (1994)). Reports of the use of bacterial RecA in association with DNA sequences to manipulate homologous target DNA, including improvement of the efficiency of gene targeting in non-plant systems, have been published (see, e.g., PCT published Patent Application Nos. WO 87/01730 and WO 93/22443).

The catalysis of in vitro pairing and strand exchange between circular viral single strand DNA ("ss DNA") and linear duplex DNA ("ds DNA") by a RAD51 recombinase from *S. cerevisiae* has also been reported (see, e.g., Sung, *Science*, 265:1241–43 (1994); Kanaar, et al., *Nature* 391:335–338 (1998); Benson, et al., *Nature* 391:401–410 (1998)). To date, work with recombinase enzymes in plants, however, has been very limited. Accordingly, there is an ongoing need for the identification and characterization of the functional activities of recombinase enzymes which may offer improved and expanded methods for use in plant systems, particularly agriculturally important crop species.

Obtaining targeted knockouts of endogenous genes through introduction of homologous strands of DNA is a feat which has been achieved in mammalian cells several years ago. It is however an enormous challenge in plants, which is indicative of a lack of sufficient knowledge about homologous recombination in plant cells. Isolation and characterization of plant genes involved in recombination may help in overcoming the present obstacles.

SUMMARY OF THE INVENTION

The present invention concerns an isolated polynucleotide comprising a nucleotide sequence selected from the group consisting of: (a) a first nucleotide sequence encoding a polypeptide of at least 50 amino acids having at least 80% identity based on the Clustal method of alignment when compared to a polypeptide of SEQ ID NO:6; (b) a second nucleotide sequence encoding a polypeptide of at least 100 amino acids having at least 80% identity based on the Clustal method of alignment when compared to a polypeptide of SEQ ID NO:2; (c) a third nucleotide sequence encoding a polypeptide of at least 250 amino acids having at least 95% identity based on the Clustal method of alignment when compared to a polypeptide of SEQ ID NO:4; (d) a fourth nucleotide sequence encoding a polypeptide of at least 340 amino acids having at least 95% identity based on the Clustal method of alignment when compared to a polypeptide of SEQ ID NO:8; and (e) a fifth nucleotide sequence comprising the complement of (a), (b), (c) or (d).

In a second embodiment, it is preferred that the isolated polynucleotide of the claimed invention comprises a first nucleotide sequence which comprises a nucleic acid sequence selected from the group consisting of SEQ ID NOs:1, 3, 5, and 7 that codes for the polypeptide selected from the group consisting of SEQ ID NOs:2, 4, 6, and 8.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a polypeptide selected from the group consisting of: (a) a polypeptide of at least 50 amino acids having at least 80% identity based on the Clustal method of alignment when compared to a polypeptide of SEQ ID NO:6; (b) a polypeptide of at least 100 amino acids having at least 80% identity based on the Clustal method of alignment when compared to a polypeptide of SEQ ID NO:2; (c) a polypeptide of at least 250 amino acids having at least 95% identity based on the Clustal method of alignment when compared to a polypeptide of SEQ ID NO:4; and (d) a polypeptide of at least 340 amino acids having at least 95% identity based on the Clustal method of alignment when compared to a polypeptide of SEQ ID NO:8.

In an eighth embodiment, the invention relates to a method of selecting an isolated polynucleotide that affects the level of expression of a RAD51 polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the RAD51 polypeptide or enzyme activity in the host cell containing the isolated polynucleotide; and (d) comparing the level of the RAD51 polypeptide or enzyme activity in the host cell containing the isolated polynucleotide with the level of the RAD51 polypeptide or enzyme activity in the host cell that does not contain the isolated polynucleotide.

In a ninth embodiment, the invention concerns a method of obtaining a nucleic acid fragment encoding a substantial portion of a RAD51 polypeptide, preferably a plant RAD51 polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a RAD51 protein amino acid sequence.

In a tenth embodiment, this invention relates to a method of obtaining a nucleic acid fragment encoding all or a substantial portion of the amino acid sequence encoding a RAD51 polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or an isolated polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the RAD51 protein polynucleotide in an amount sufficient to complement a null mutant to provide a positive selection means.

BRIEF DESCRIPTION OF THE DRAWING AND SEQUENCE LISTING

The invention can be more fully understood from the following detailed description, the accompanying drawing, and the Sequence Listing which form a part of this application.

FIGS. 1A–1B depict the amino acid sequence alignment between the RAD51 proteins encoded by the nucleotide sequences derived from soybean clone ssm.pk0068.g1 (SEQ ID NO:4), and wheat clone wkm1c.pk0003.b8 (SEQ ID NO:8), the *Arabidopsis thaliana* RAD51 sequence (NCBI GenBank Identifier (GI) No. 1706947; SEQ ID NO:9) and the *Zea mays* RAD51A sequence (NCBI GenBank Identifier (GI) No. 4886752; SEQ ID NO:10). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding at a minimum the mature protein derived from an EST, FIS, a contig, or an FIS and PCR ("CGS"). Nucleotide SEQ ID NOs:1 and 5 correspond to nucleotide SEQ ID NOs:3 and 5, respectively, presented in U.S. Provisional Application No. 60/133,438, filed May 11, 1999. Amino acid SEQ ID NOs:2 and 6 correspond to amino acid SEQ ID NOs:4 and 6, respectively, presented in U.S. Provisional Application No. 60/133,438, filed May 11, 1999. The sequence descriptions and Sequence Listing attached hereto comply with the rules governing nucleotide and/or amino acid sequence disclosures in patent applications as set forth in 37 C.F.R §1.821–1.825.

TABLE 1

Recombination Proteins

| Protein (Plant Source) | Clone Designation | Status | SEQ ID NO: (Nucleotide) | (Amino Acid) |
|---|---|---|---|---|
| RAD51 (Soybean) | ssm.pk0068.g1 | EST | 1 | 2 |
| RAD51 (Soybean) | ssm.pk0068.g1(FIS) | CGS | 3 | 4 |
| RAD51 (Wheat) | wkm1c.pk0003.b8 | EST | 5 | 6 |
| RAD51 (Wheat) | wkm1c.pk0003.b8(FIS) | CGS | 7 | 8 |

The Sequence Listing contains the one letter code for nucleotide sequence characters and the three letter codes for amino acids as defined in conformity with the IUPAC-IUBMB standards described in Nucleic Acids Res. 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, and 7, or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7, and the complement of such nucleotide sequences may be used in methods of selecting an isolated polynucleotide that affects the expression of a RAD51 polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min. and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 or 340 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WTNDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" refers to a post-translationally processed polypeptide; i.e., one from which any pre- or propeptides present in the primary translation product have been removed. "Precursor protein" refers to the primary product of translation of mRNA; i.e., with pre- and propeptides still present Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) Meth. Enzymol. 143:277) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al., *Molecular Cloning: A Laboratory Manual*; Cold Spring Harbor Laboratory Press: Cold Spring Harbor, 1989 (hereinafter "Maniatis").

"PCR" or "polymerase chain reaction" is a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 50 amino acids having at least 80% identity based on the Clustal method of alignment when compared to a polypeptide of SEQ ID NO:6; (b) a second nucleotide sequence encoding a polypeptide of at least 100 amino acids having at least 80% identity based on the Clustal method of alignment when compared to a polypeptide of SEQ ID NO:2; (c) a third nucleotide sequence encoding a polypeptide of at least 250 amino acids having at least 95% identity based on the Clustal method of alignment when compared to a polypeptide of SEQ ID NO:4; (d) a fourth nucleotide sequence encoding a polypeptide of at least 340 amino acids having at least 95% identity based on the Clustal method of alignment when compared to a polypeptide of SEQ ID NO:8; and (e) a fifth nucleotide sequence comprising the complement of (a), (b), (c) or (d).

Preferably, the first nucleotide sequence comprises a nucleic acid sequence selected from the group consisting of SEQ ID NOs:1, 3, 5, and 7, that codes for the polypeptide selected from the group consisting of SEQ ID NOs:2, 4, 6, and 8.

Nucleic acid fragments encoding at least a substantial portion of several recombination proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other RAD51 proteins, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequence (s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the rRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Nat. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, and 7 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a RAD51 polypeptide, preferably a substantial portion of a plant RAD51 polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:3, 5, and 7, and the complement of such nucleotide sequences, and amplifying a nucleic acid fragment (preferably a cDNA inserted in a cloning vector) using the oligonucleotide primer. The amplified nucleic acid fragment preferably will encode a substantial portion of a RAD51 polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of recombination in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide selected from the group consisting of: (a) a polypeptide of at least 50 amino acids having at least 80% identity based on the Clustal method of alignment when compared to a polypeptide of SEQ ID NO:6; (b) a polypeptide of at least 100 amino acids having at least 80% identity based on the Clustal method of alignment when compared to a polypeptide of SEQ ID NO:2; (c) a polypeptide of at least 250 amino acids having at least 95% identity based on the Clustal method of alignment when compared to a polypeptide of SEQ ID NO:4; and (d) a polypeptide of at least 340 amino acids having at least 95% identity based on the Clustal method of alignment when compared to a polypeptide of SEQ ID NO:8.

The instant polypeptides (or portions thereof) may be produced in heterologous host cells, particularly in the cells of microbial hosts, and can be used to prepare antibodies to the proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded recombination protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl.*

Acad. Sci USA 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

EXAMPLE 1

Composition of cDNA Libraries, Isolation and Sequencing of cDNA Clones cDNA libraries representing mRNAs from various soybean (Glycine ma) and wheat (*Triticum aestivum*) tissues were prepared. The characteristics of the libraries are described below.

TABLE 2 cDNA Libraries from Soybean and Wheat

| Library | Tissue | Clone |
|---------|--------|-------|
| ssm | Soybean Shoot Meristem | ssm.pk0068.g1 |
| wkm1c | Wheat Kernel Malted 55 Hours at 22° C. | wkm1c.pk0003.b8 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

Identification of cDNA Clones cDNA clones encoding recombination protein were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

EXAMPLE 3

Characterization of cDNA Clones Encoding RAD51 Protein

The BLASTX search using the EST sequences from clones ssm.pk0068.g1 and wkm1c.pkOOO3.b8 revealed similarity of the proteins encoded by the cDNAs to RAD51 protein from *Arabidopsis thaliana* (NCBI Gene Identifier No. 1706947). The BLAST results for each of these sequences are shown in Table 3:

TABLE 3

BLAST Results for Clones Encoding Polypeptides
Homologous to RAD51 Protein

| Clone | BLAST pLog Score 1706947 |
|---|---|
| ssm.pk0068.g1 | 58.70 |
| wkm1c.pk0003.b8 | 16.52 |

The sequence of a substantial portion of the cDNA insert from clone ssm.pk0068.g1 is shown in SEQ ID NO:1; the deduced amino acid sequence of this substantial portion of the cDNA is shown in SEQ ID NO:2. The sequence of a substantial portion of the cDNA insert from clone wkm1c.pk0003.b8 is shown in SEQ ID NO:5; the deduced amino acid sequence of this substantial portion of the cDNA is shown in SEQ ID NO:6. BLAST scores and probabilities indicate that the instant nucleic acid fragments encode substantial portions of corn, soybean and wheat RAD51 proteins. A corn RAD51 sequence has been described previously (PCT published Patent Application No. WO 99/41394-A1).

The BLASTX search using the sequences from clones listed in Table 4 revealed similarity of the polypeptides encoded by the cDNAs to RAD51 from *Arabidopsis thaliana* (NCBI GenBank Identifier (GI) No. 1706947; SEQ ID NO:9) and *Zea mays* (NCBI GenBank Identifier (01) No. 4886752; SEQ ID NO:10). Shown in Table 4 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides
Homologous to RAD51

| | | BLAST Results | |
|---|---|---|---|
| Clone | Status | NCBI GenBank Identifier (GI) No. | pLog Score |
| ssm.pk0068.g1(FIS) | CGS | 1706947 | 173.00 |
| wkm1c.pk0003.b8(FIS) | CGS | 4886752 | 179.00 |

FIGS. 1A–1B present an alignment of the amino acid sequences set forth in SEQ ID NOs: 4 and 8, the *Arabidopsis thaliana* sequence (NCBI GenBank Identifier (GI) No. 1706947; SEQ ID NO:9) and the *Zea mays* sequence (NCBI GenBank Identifier (GI) No. 4886752; SEQ ID NO:10). The data in Table 5 represents a calculation of the percent identity of the amino acid sequences set forth in SEQ ID NOs: 4 and 8, the *Arabidopsis thaliana* sequence (NCBI GenBank Identifier (GI) No. 1706947; SEQ ID NO:9) and the *Zea mays* sequence (NCBI GenBank Identifier (GI) No. 4886752; SEQ ID NO:10).

TABLE 5

Percent Identity of Amino Acid Sequences Deduced From the
Nucleotide Sequences of cDNA Clones Encoding Polypeptides
Homologous to RAD51

| | Percent Identity to | |
|---|---|---|
| SEQ ID NO. | SEQ ID NO:9 | SEQ ID NO:10 |
| 4 | 87.4 | 85.6 |
| 8 | 85.4 | 89.7 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode entire RAD51 protein.

EXAMPLE 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 5

Expression of Chimeric Genes in Dicot Cells

A seed-specific construct composed of the promoter and transcription terminator from the gene encoding the 0 subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed construct comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 mL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

EXAMPLE 7

Assaying Recombination Protein Activity

The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays to verify over- or underexpression of recombination proteins disclosed herein in functional form in transgenic plants and transformed bacterial cells. Assays may be conducted under well known experimental conditions which permit optimal enzymatic activity. For example, assays for RAD51 are presented by Sung, P., (1994) *Science* 265:1241–1243

What is claimed is:

1. An isolated polynucleotide comprising:
   (a) a nucleotide sequence encoding a polypeptide with RAD51 recombinase activity, wherein the polypeptide has an amino acid sequence of at least 95% sequence identity, based on the Clustal V method of alignment, when compared to one of SEQ ID NO:8, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide comprises one of SEQ ID NO:8.

3. The polynucleotide of claim 1, wherein the nucleotide sequence comprises one of SEQ ID NO:7.

4. A vector comprising the polynucleotide of claim 1.

5. A recombinant DNA construct comprising the polynucleotide of claim 1 operably linked to at least one regulatory sequence.

6. A method for transforming a cell, comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

SEQUENCE LISTING

```
<160> NUMBER OF SEQ ID NOS: 10

<210> SEQ ID NO 1
<211> LENGTH: 568
<212> TYPE: DNA
<213> ORGANISM: Glycine max
<220> FEATURE:
<221> NAME/KEY: unsure
<222> LOCATION: (19)

<400> SEQUENCE: 1
cttttgaatc ctcatcacnc ccactccacc catctcatct ctcttcgatc ttaaatattg     60
aatctttgag gggtcagaat cagaatgtcg gcaaccatgg agcagcaacg ccaccaaaaa    120
gcgccccaac aacaagacga agccgaagag atacaacctg gcccttacc  cgtcgagcaa    180 cttcaggcat cgggcatagc cgccacggac gttaagaagc ttaaagacgc cggaatttgc    240
accgttgaat ccgttgctta cactcctagg aaagaccttt tgcaaatcaa aggtatcagt    300
gaagctaaag ttgacaagat cattgaagca gcttctaagc tggtgcctat gggtttcacc    360
agcgctagtg aacttcatgc ccagcgcgat gcaatcattc agataaccac gggatcaaga    420
gagttgacaa gatattggag ggtggagttg agaccggttc tataactgat tatatggtga    480
attcggtctg ggaagactca gttgtgtcac actctctgtg tcacttgcaa ttgccactag    540
accaaggagg tggggagggt aaactatt                                       568

<210> SEQ ID NO 2
<211> LENGTH: 113
<212> TYPE: PRT
<213> ORGANISM: Glycine max

<400> SEQUENCE: 2

Thr Met Glu Gln Gln Arg His Gln Lys Ala Pro Gln Gln Gln Asp Glu
  1               5                  10                  15

Ala Glu Glu Ile Gln Pro Gly Pro Leu Pro Val Glu Gln Leu Gln Ala
             20                  25                  30

Ser Gly Ile Ala Ala Thr Asp Val Lys Lys Leu Lys Asp Ala Gly Ile
         35                  40                  45

Cys Thr Val Glu Ser Val Ala Tyr Thr Pro Arg Lys Asp Leu Leu Gln
     50                  55                  60

Ile Lys Gly Ile Ser Glu Ala Lys Val Asp Lys Ile Ile Glu Ala Ala
 65                  70                  75                  80

Ser Lys Leu Val Pro Met Gly Phe Thr Ser Ala Ser Glu Leu His Ala
                 85                  90                  95
```

Gln Arg Asp Ala Ile Ile Gln Ile Thr Thr Gly Ser Arg Glu Leu Thr
                100                 105                 110

Arg

<210> SEQ ID NO 3
<211> LENGTH: 1219
<212> TYPE: DNA
<213> ORGANISM: Glycine max

<400> SEQUENCE: 3
gcacgagctt tgaatcctc atcacccca ctccacccat ctcatctctc ttcgatctta      60
aatattgaat ctttgagggg tcagaatcag aatgtcggca accatggagc agcaacgcca     120
ccaaaaagcg ccccaacaac aagacgaagc cgaagagata caacctggcc ctttacccgt     180
cgagcaactt caggcatcgg gcatagccgc cacggacgtt aagaagctta agacgccgg      240
aatttgcacc gttgaatccg ttgcttacac tcctaggaaa gacctttgc aaatcaaagg      300
tatcagtgaa gctaaagttg acaagatcat tgaagcagct tctaagctgg tgcctatggg     360
tttcaccagc gctagtgaac ttcatgccca gcgcgatgca atcattcaga taaccacggg     420
atcaagagag cttgacaaga tattggaggg tggagttgag accggttcta taactgaatt     480
atatggtgaa tttcggtctg ggaagactca gttgtgtcac actctctgtg tcacttgcca     540
attgccacta gaccaaggag gtggggaggg taaagctatg tacatagatg ctgagggcac     600
atttaggcct cagcgactct acagatagc agataggttt ggattgaatg tgttgatgt      660
attggaaaat gttgcttatg ctagagcata caatactgat catcaatcac ggcttctgct     720
tgaagcagct tcaatgatgg tggaaactag gtttgctgta atgatagtag atagtgctac     780
tgccctctat aggacagatt tttctggaag gggggagctt tcagctcggc aaatgcatct     840
agcaaagttc ctgaggagcc ttcagaaatt agcagatgag tttggtgtgg ctattgtcat     900
aacaaaccaa gtagtttcac aagtagatgg ttctgcagtc tttgctggac ctcaaatcaa     960
gcctattgga ggcaacatta tggctcatgc tacaacaacg aggctagctc tcaggaaagg    1020
gagagggaa gagcgaatct gtaaagtgat aagttctcct tgcttggcgg aagccgaagc    1080
aaggtttcag atttgtgccg aaggagtttc agatgttaaa gactaactga tttcagaatg    1140
tttgaatttt tctgtatggt atacctgtcg atttgcaagt atccagtatt aaattttgca    1200
aaaaaaaaaa aaaaaaaa                                                 1219

<210> SEQ ID NO 4
<211> LENGTH: 344
<212> TYPE: PRT
<213> ORGANISM: Glycine max

<400> SEQUENCE: 4

Met Ser Ala Thr Met Glu Gln Gln Arg His Gln Lys Ala Pro Gln Gln
 1               5                  10                  15

Gln Asp Glu Ala Glu Glu Ile Gln Pro Gly Pro Leu Pro Val Glu Gln
                20                  25                  30

Leu Gln Ala Ser Gly Ile Ala Ala Thr Asp Val Lys Lys Leu Lys Asp
            35                  40                  45

Ala Gly Ile Cys Thr Val Glu Ser Val Ala Tyr Thr Pro Arg Lys Asp
        50                  55                  60

Leu Leu Gln Ile Lys Gly Ile Ser Glu Ala Lys Val Asp Lys Ile Ile
65                  70                  75                  80

-continued

```
Glu Ala Ala Ser Lys Leu Val Pro Met Gly Phe Thr Ser Ala Ser Glu
                85                  90                  95
Leu His Ala Gln Arg Asp Ala Ile Ile Gln Ile Thr Thr Gly Ser Arg
            100                 105                 110
Glu Leu Asp Lys Ile Leu Glu Gly Gly Val Glu Thr Gly Ser Ile Thr
        115                 120                 125
Glu Leu Tyr Gly Glu Phe Arg Ser Gly Lys Thr Gln Leu Cys His Thr
    130                 135                 140
Leu Cys Val Thr Cys Gln Leu Pro Leu Asp Gln Gly Gly Gly Glu Gly
145                 150                 155                 160
Lys Ala Met Tyr Ile Asp Ala Glu Gly Thr Phe Arg Pro Gln Arg Leu
                165                 170                 175
Leu Gln Ile Ala Asp Arg Phe Gly Leu Asn Gly Val Asp Val Leu Glu
            180                 185                 190
Asn Val Ala Tyr Ala Arg Ala Tyr Asn Thr Asp His Gln Ser Arg Leu
        195                 200                 205
Leu Leu Glu Ala Ala Ser Met Met Val Glu Thr Arg Phe Ala Val Met
    210                 215                 220
Ile Val Asp Ser Ala Thr Ala Leu Tyr Arg Thr Asp Phe Ser Gly Arg
225                 230                 235                 240
Gly Glu Leu Ser Ala Arg Gln Met His Leu Ala Lys Phe Leu Arg Ser
                245                 250                 255
Leu Gln Lys Leu Ala Asp Glu Phe Gly Val Ala Ile Val Ile Thr Asn
            260                 265                 270
Gln Val Val Ser Gln Val Asp Gly Ser Ala Val Phe Ala Gly Pro Gln
        275                 280                 285
Ile Lys Pro Ile Gly Gly Asn Ile Met Ala His Ala Thr Thr Thr Arg
    290                 295                 300
Leu Ala Leu Arg Lys Gly Arg Gly Glu Glu Arg Ile Cys Lys Val Ile
305                 310                 315                 320
Ser Ser Pro Cys Leu Ala Glu Ala Glu Ala Arg Phe Gln Ile Cys Ala
                325                 330                 335
Glu Gly Val Ser Asp Val Lys Asp
            340
```

```
<210> SEQ ID NO 5
<211> LENGTH: 560
<212> TYPE: DNA
<213> ORGANISM: Triticum aestivum
<220> FEATURE:
<221> NAME/KEY: unsure
<222> LOCATION: (103)
<221> NAME/KEY: unsure
<222> LOCATION: (108)
<221> NAME/KEY: unsure
<222> LOCATION: (278)
<221> NAME/KEY: unsure
<222> LOCATION: (328)
<221> NAME/KEY: unsure
<222> LOCATION: (338)..(339)
<221> NAME/KEY: unsure
<222> LOCATION: (342)
<221> NAME/KEY: unsure
<222> LOCATION: (354)
<221> NAME/KEY: unsure
<222> LOCATION: (367)
<221> NAME/KEY: unsure
<222> LOCATION: (376)
<221> NAME/KEY: unsure
<222> LOCATION: (380)
<221> NAME/KEY: unsure
<222> LOCATION: (414)
```

-continued

```
<221> NAME/KEY: unsure
<222> LOCATION: (419)
<221> NAME/KEY: unsure
<222> LOCATION: (429)
<221> NAME/KEY: unsure
<222> LOCATION: (464)
<221> NAME/KEY: unsure
<222> LOCATION: (472)
<221> NAME/KEY: unsure
<222> LOCATION: (474)
<221> NAME/KEY: unsure
<222> LOCATION: (486)..(487)
<221> NAME/KEY: unsure
<222> LOCATION: (507)
<221> NAME/KEY: unsure
<222> LOCATION: (511)
<221> NAME/KEY: unsure
<222> LOCATION: (516)
<221> NAME/KEY: unsure
<222> LOCATION: (522)
<221> NAME/KEY: unsure
<222> LOCATION: (529)
<221> NAME/KEY: unsure
<222> LOCATION: (537)..(538)..(539)
<221> NAME/KEY: unsure
<222> LOCATION: (547)
<221> NAME/KEY: unsure
<222> LOCATION: (549)
<221> NAME/KEY: unsure
<222> LOCATION: (551)

<400> SEQUENCE: 5
gagaaacgcc tcacatcccg agcatctctc tgtctcttcg agtggtgggc cccatgtcgt     60
cggcggcggc gcaccagaag gcggccgcgg cggctctccg aanggaanga ggaggccggg    120
gagcacgggc ctttccccat cgagcacctc caggcatctg aatagctgc agttgatgtg    180
aaaaagtcaa agatgctggt ctttgcacag tggatctgta gcttatctcc aaggaaagat    240
tttttgcaaa ttaaagggat tagtgaaacc aaagtccnat aagataattt aagcacttcc    300
aatttggttc aactgggatt tactaatnct accaattnna ancgcaaagg tccnaattt     360
cccaagnttt caacangttn aagagaactt tataaatatt ggagggaaga atanaacang    420
tttatcacng actttatggg gatttaagtc tgggaaacca tttngccaac cncngttcaa    480
agtaanncca atggacaagg ggtggtnaag naaggnttta anttaccana aggaatnnng    540
ccaaaananc ncaaatacaa                                                 560

<210> SEQ ID NO 6
<211> LENGTH: 69
<212> TYPE: PRT
<213> ORGANISM: Triticum aestivum
<220> FEATURE:
<221> NAME/KEY: UNSURE
<222> LOCATION: (10)..(11)
<221> NAME/KEY: UNSURE
<222> LOCATION: (48)..(49)..(50)..(51)
<221> NAME/KEY: UNSURE
<222> LOCATION: (69)

<400> SEQUENCE: 6

Arg Arg Arg Pro Arg Arg Leu Ser Glu Xaa Xaa Glu Glu Ala Gly Glu
 1               5                  10                  15

His Gly Pro Phe Pro Ile Glu His Leu Gln Ala Ser Gly Ile Ala Ala
                20                  25                  30

Val Asp Val Glu Lys Val Lys Asp Ala Gly Leu Cys Thr Val Asp Xaa
            35                  40                  45

Xaa Xaa Xaa Ser Pro Arg Lys Asp Phe Leu Gln Ile Lys Gly Ile Ser
 50                  55                  60
```

Glu Thr Lys Val Xaa
 65

<210> SEQ ID NO 7
<211> LENGTH: 1585
<212> TYPE: DNA
<213> ORGANISM: Triticum aestivum

<400> SEQUENCE: 7

| | | | | | |
|---|---|---|---|---|---:|
| gcacgaggag | aaacgcctca | catcccgagc | atctctctgt | ctcttcgagt ggtgggcccc | 60 |
| atgtcgtcgg | cggcggcgca | ccagaaggcg | gccgcggcgg | ctcccgtcga ggaggaggag | 120 |
| gccggggagc | acgggccttt | ccccatcgag | cacctccagg | catctggaat agctgcagtt | 180 |
| gatgtgaaaa | agctcaaaga | tgctggtctt | gcacagtgg | agtctgtagc ttattctcca | 240 |
| aggaaagatc | ttttgcaaat | taaagggatt | agtgaagcca | agtcgataa gataattgaa | 300 |
| gcagcttcga | agttggttcc | actgggattt | actagtgcta | cccaacttca tgcgcagagg | 360 |
| ctcgagatta | tccaagttac | aacaggatca | agagaacttg | ataaaatatt ggagggagga | 420 |
| atagaaacag | gatctatcac | ggagctttat | ggtgaattta | ggtctgggaa gactcagttg | 480 |
| tgccatactc | tctgtgtcac | atgtcagctc | ccactggacc | aaggtggtgg tgaaggaaag | 540 |
| gctctttata | ttgacgcaga | aggcacattc | agaccacaaa | gactcctcca gatagcagac | 600 |
| aggtgatatc | gcagtttttt | ctttctatac | cagtttaaat | tattattcat tctgccacta | 660 |
| tgcggtgtat | gattgaacag | ctaaacaaga | taatcctgta | ttttaggttt ggactgaatg | 720 |
| gtgctgatgt | acttgagaat | gtagcttatg | ctagagcata | taatactgat catcaatcaa | 780 |
| gacttctgct | ggaagcagct | tccatgatgg | tggagacaag | gtttgcgctt atggttatag | 840 |
| atagtgccac | agccttatac | agaactgact | tctctggtag | aggggagcta tcagcaaggc | 900 |
| aaatgcatct | ggccaagttt | ctcaggagcc | ttcagaaatt | agcggatgag ttcggggtgg | 960 |
| cagtggtaat | ctccaaccag | gtagtggccc | aagtggatgg | tggtgcaatg tttgctgggc | 1020 |
| cacagatcaa | acccattgga | gggaacatca | tggctcatgc | ttccacgacg aggctttatc | 1080 |
| tccgtaaggg | aagggcggag | gagcggatct | gtaaggtggt | gagctctccc tgcctggctg | 1140 |
| aagctgaagc | aaggtttcag | atatcacctg | aaggcgtcac | agatgttaag gattgagagt | 1200 |
| gttctttgct | tgtcatgggg | atacctcgtg | tatcagactt | agcctgctgt ttgcatcttc | 1260 |
| agcaacagat | gctagcttgt | gccgatgaaa | gaaggcccct | ctgtatagca aacaccctgc | 1320 |
| agctgcagtg | gcaccatagg | ggctccctgg | aaggaaatgt | tgtacagcta atctcccata | 1380 |
| gtttgcttgt | tctatctttt | ttagtggtct | tagtatgcac | tgctctcatc aagatcgtta | 1440 |
| tggttatggc | tgagtgatgg | gaaaatgtag | ttgctcactt | tgtttcaaat atccttggtc | 1500 |
| atctaggaca | ttgacattgc | ctcctatgtg | atattggacc | accaatttct ttgacaatat | 1560 |
| gttagataaa | aaaaaaaaaa | aaaaa | | | 1585 |

<210> SEQ ID NO 8
<211> LENGTH: 343
<212> TYPE: PRT
<213> ORGANISM: Triticum aestivum

<400> SEQUENCE: 8

Met Ser Ser Ala Ala His Gln Lys Ala Ala Ala Ala Pro Val
 1               5                  10                  15

Glu Glu Glu Glu Ala Gly Glu His Gly Pro Phe Pro Ile Glu His Leu
             20                  25                  30

```
Gln Ala Ser Gly Ile Ala Ala Val Asp Val Lys Lys Leu Lys Asp Ala
             35                  40                  45

Gly Leu Cys Thr Val Glu Ser Val Ala Tyr Ser Pro Arg Lys Asp Leu
 50                  55                  60

Leu Gln Ile Lys Gly Ile Ser Glu Ala Lys Val Asp Lys Ile Ile Glu
 65                  70                  75                  80

Ala Ala Ser Lys Leu Val Pro Leu Gly Phe Thr Ser Ala Thr Gln Leu
                 85                  90                  95

His Ala Gln Arg Leu Glu Ile Ile Gln Val Thr Thr Gly Ser Arg Glu
            100                 105                 110

Leu Asp Lys Ile Leu Glu Gly Ile Glu Thr Gly Ser Ile Thr Glu
            115                 120                 125

Leu Tyr Gly Glu Phe Arg Ser Gly Lys Thr Gln Leu Cys His Thr Leu
130                 135                 140

Cys Val Thr Cys Gln Leu Pro Leu Asp Gln Gly Gly Gly Glu Gly Lys
145                 150                 155                 160

Ala Leu Tyr Ile Asp Ala Glu Gly Thr Phe Arg Pro Gln Arg Leu Leu
                165                 170                 175

Gln Ile Ala Asp Arg Phe Gly Leu Asn Gly Ala Asp Val Leu Glu Asn
            180                 185                 190

Val Ala Tyr Ala Arg Ala Tyr Asn Thr Asp His Gln Ser Arg Leu Leu
            195                 200                 205

Leu Glu Ala Ala Ser Met Met Val Glu Thr Arg Phe Ala Leu Met Val
210                 215                 220

Ile Asp Ser Ala Thr Ala Leu Tyr Arg Thr Asp Phe Ser Gly Arg Gly
225                 230                 235                 240

Glu Leu Ser Ala Arg Gln Met His Leu Ala Lys Phe Leu Arg Ser Leu
                245                 250                 255

Gln Lys Leu Ala Asp Glu Phe Gly Val Ala Val Val Ile Ser Asn Gln
            260                 265                 270

Val Val Ala Gln Val Asp Gly Gly Ala Met Phe Ala Gly Pro Gln Ile
            275                 280                 285

Lys Pro Ile Gly Gly Asn Ile Met Ala His Ala Ser Thr Thr Arg Leu
290                 295                 300

Tyr Leu Arg Lys Gly Arg Ala Glu Glu Arg Ile Cys Lys Val Val Ser
305                 310                 315                 320

Ser Pro Cys Leu Ala Glu Ala Glu Ala Arg Phe Gln Ile Ser Pro Glu
                325                 330                 335

Gly Val Thr Asp Val Lys Asp
            340
```

<210> SEQ ID NO 9
<211> LENGTH: 342
<212> TYPE: PRT
<213> ORGANISM: Arabidopsis thaliana

<400> SEQUENCE: 9

```
Met Thr Thr Met Glu Gln Arg Arg Asn Gln Asn Ala Val Gln Gln Gln
 1               5                  10                  15

Asp Asp Glu Glu Thr Gln His Gly Pro Phe Pro Val Glu Gln Leu Gln
                 20                  25                  30

Ala Ala Gly Ile Ala Ser Val Asp Val Lys Lys Leu Arg Asp Ala Gly
             35                  40                  45

Leu Cys Thr Val Glu Gly Val Ala Tyr Thr Pro Arg Lys Asp Leu Leu
```

-continued

```
                50                  55                  60
Gln Ile Lys Gly Ile Ser Asp Ala Lys Val Asp Lys Ile Val Glu Ala
 65                  70                  75                  80
Ala Ser Lys Leu Val Pro Leu Gly Phe Thr Ser Ala Ser Gln Leu His
                 85                  90                  95
Ala Gln Arg Gln Glu Ile Ile Gln Ile Thr Ser Gly Ser Arg Glu Leu
                100                 105                 110
Asp Lys Val Leu Glu Gly Gly Ile Glu Thr Gly Ser Ile Thr Glu Leu
                115                 120                 125
Tyr Gly Glu Phe Arg Ser Gly Lys Thr Gln Leu Cys His Thr Leu Cys
130                 135                 140
Val Thr Cys Gln Leu Pro Met Asp Gln Gly Gly Glu Gly Lys Ala
145                 150                 155                 160
Met Tyr Ile Asp Ala Glu Gly Thr Phe Arg Pro Gln Arg Leu Leu Gln
                165                 170                 175
Ile Ala Asp Arg Phe Gly Leu Asn Gly Ala Asp Val Leu Glu Asn Val
                180                 185                 190
Ala Tyr Ala Arg Ala Tyr Asn Thr Asp His Gln Ser Arg Leu Leu Leu
                195                 200                 205
Glu Ala Ala Ser Met Met Ile Glu Thr Arg Phe Ala Leu Leu Ile Val
                210                 215                 220
Asp Ser Ala Thr Ala Leu Tyr Arg Thr Asp Phe Ser Gly Arg Gly Glu
225                 230                 235                 240
Leu Ser Ala Arg Gln Met His Leu Ala Lys Phe Leu Arg Ser Leu Gln
                245                 250                 255
Lys Leu Ala Asp Glu Phe Gly Val Ala Val Val Ile Thr Asn Gln Val
                260                 265                 270
Val Ala Gln Val Asp Gly Ser Ala Leu Phe Ala Gly Pro Gln Phe Lys
                275                 280                 285
Pro Ile Gly Gly Asn Ile Met Ala His Ala Thr Thr Thr Arg Leu Ala
                290                 295                 300
Leu Arg Lys Gly Arg Ala Glu Glu Arg Ile Cys Lys Val Ile Ser Ser
305                 310                 315                 320
Pro Cys Leu Pro Glu Ala Glu Ala Arg Phe Gln Ile Ser Thr Glu Gly
                325                 330                 335
Val Thr Asp Cys Lys Asp
                340

<210> SEQ ID NO 10
<211> LENGTH: 340
<212> TYPE: PRT
<213> ORGANISM: Zea mays

<400> SEQUENCE: 10

Met Ser Ser Ala Ala Gln Gln Gln Lys Ala Ala Ala Glu Gln
 1               5                  10                  15
Glu Glu Val Glu His Gly Pro Phe Pro Ile Glu Gln Leu Gln Ala Ser
                 20                  25                  30
Gly Ile Ala Ala Leu Asp Val Lys Lys Leu Lys Asp Ser Gly Leu His
                 35                  40                  45
Thr Val Glu Ala Val Ala Tyr Thr Pro Arg Lys Asp Leu Leu Gln Ile
                 50                  55                  60
Lys Gly Ile Ser Glu Ala Lys Ala Asp Lys Ile Ile Glu Ala Ala Ser
 65                  70                  75                  80
```

-continued

```
Lys Ile Val Pro Leu Gly Phe Thr Ser Ala Ser Gln Leu His Ala Gln
             85                  90                  95

Arg Leu Glu Ile Ile Gln Val Thr Thr Gly Ser Arg Glu Leu Asp Lys
            100                 105                 110

Ile Leu Glu Gly Gly Ile Glu Thr Gly Ser Ile Thr Glu Ile Tyr Gly
            115                 120                 125

Glu Phe Arg Ser Gly Lys Thr Gln Leu Cys His Thr Pro Cys Val Thr
        130                 135                 140

Cys Gln Leu Pro Leu Asp Gln Gly Gly Glu Gly Lys Ala Leu Tyr
145                 150                 155                 160

Ile Asp Ala Glu Gly Thr Phe Arg Pro Gln Arg Leu Leu Gln Ile Ala
            165                 170                 175

Asp Arg Phe Gly Leu Asn Gly Ala Asp Val Leu Glu Asn Val Ala Tyr
            180                 185                 190

Ala Arg Ala Tyr Asn Thr Asp His Gln Ser Arg Leu Leu Leu Glu Ala
        195                 200                 205

Ala Ser Met Met Ile Glu Thr Arg Phe Ala Leu Met Val Val Asp Ser
210                 215                 220

Ala Thr Ala Leu Tyr Arg Thr Asp Phe Ser Gly Arg Gly Glu Leu Ser
225                 230                 235                 240

Ala Arg Gln Met His Met Ala Lys Phe Leu Arg Ser Leu Gln Lys Leu
            245                 250                 255

Ala Asp Glu Phe Gly Val Ala Val Val Ile Thr Asn Gln Val Val Ala
            260                 265                 270

Gln Val Asp Gly Ser Ala Met Phe Ala Gly Pro Gln Phe Lys Pro Ile
        275                 280                 285

Gly Gly Asn Ile Met Ala His Ala Ser Thr Thr Arg Leu Ala Leu Arg
        290                 295                 300

Lys Gly Arg Gly Glu Glu Arg Ile Cys Lys Val Ile Ser Ser Pro Cys
305                 310                 315                 320

Leu Ala Glu Ala Glu Ala Arg Phe Gln Leu Ala Ser Glu Gly Ile Ala
            325                 330                 335

Asp Val Lys Asp
            340
```